(12) United States Patent
Looser et al.

(10) Patent No.: US 10,082,516 B2
(45) Date of Patent: Sep. 25, 2018

(54) RELATIVE HUMIDITY CONTROL APPARATUS

(71) Applicant: TECAN Schweiz AG, Mannedorf (CH)

(72) Inventors: Werner Looser, Wetzikon (CH); Erna Becker, Monchaltdorf (CH); Pius Fink, Hombrechtikon (CH); Marcel Aschwanden, Eschenbach (CH); Fredy Tanner, Stafa (CH)

(73) Assignee: TECAN SCHWEIZ AG, Mannedorf (CH)

( * ) Notice: Subject to any disclaimer, the term of this patent is extended or adjusted under 35 U.S.C. 154(b) by 48 days.

(21) Appl. No.: 15/210,543

(22) Filed: Jul. 14, 2016

(65) Prior Publication Data
US 2017/0030937 A1    Feb. 2, 2017

(30) Foreign Application Priority Data
Jul. 29, 2015    (CH) ...................... 1102/15

(51) Int. Cl.
| | |
|---|---|
| *G05B 21/00* | (2006.01) |
| *G01N 35/00* | (2006.01) |
| *G01N 33/53* | (2006.01) |
| *G01N 33/543* | (2006.01) |
| *B01L 7/00* | (2006.01) |
| *G01N 35/04* | (2006.01) |
| *G01N 35/10* | (2006.01) |

(52) U.S. Cl.
CPC .......... *G01N 35/00029* (2013.01); *B01L 7/00* (2013.01); *G01N 33/5304* (2013.01); *G01N 33/54386* (2013.01); *G01N 35/00* (2013.01); *G01N 35/0099* (2013.01); *G01N 35/00871* (2013.01); *G01N 2035/00148* (2013.01); *G01N 2035/00356* (2013.01); *G01N 2035/00455* (2013.01); *G01N 2035/0418* (2013.01); *G01N 2035/0437* (2013.01); *G01N 2035/1034* (2013.01)

(58) Field of Classification Search
CPC .... G01N 1/10; G01N 21/00; G01N 35/00029; G05B 21/00; B01L 7/00
USPC .............. 422/62, 81; 436/180; 700/274, 266
See application file for complete search history.

(56) References Cited

U.S. PATENT DOCUMENTS

| | | | |
|---|---|---|---|
| 2006/0213508 A1* | 9/2006 | Murray | ............... B05B 17/0615 128/200.16 |
| 2007/0051906 A1* | 3/2007 | Brennan | ............... G01N 17/002 250/504 R |
| 2008/0041428 A1* | 2/2008 | Morselli | ............... B05B 15/555 134/105 |

(Continued)

*Primary Examiner* — Brian J. Sines
(74) *Attorney, Agent, or Firm* — Notaro, Michalos & Zaccaria P.C.

(57) ABSTRACT

A relative humidity control apparatus for control of the relative humidity in a gas space has a nebulizer source with an outlet for nebulized liquid, a frame surrounding an open area and comprising an opening arrangement to the open area and in operational flow connection with the outlet, and a flow drive arrangement generating a gas flow from the outlet to and out of the opening arrangement. A liquid handling robot comprising this apparatus, a method of operating the apparatus, an immunoassay method and methods of controlling the time course of the relative humidity in a gaseous space and of producing a predetermined volume of a liquid are also disclosed.

17 Claims, 4 Drawing Sheets

(56) References Cited

U.S. PATENT DOCUMENTS

| | | | |
|---|---|---|---|
| 2011/0057045 A1* | 3/2011 | Narikawa | F24F 3/1405 |
| | | | 236/44 A |
| 2013/0249124 A1* | 9/2013 | Staniforth | F24F 3/16 |
| | | | 261/128 |
| 2014/0196880 A1* | 7/2014 | Pinchuk | A01G 9/246 |
| | | | 165/222 |
| 2017/0321915 A1* | 11/2017 | Staniforth | F24F 6/14 |

* cited by examiner

RELATIVE HUMIDITY CONTROL APPARATUS

The invention addressed herein relates to a relative humidity control apparatus. Under further aspects, the invention relates to a liquid handling robot comprising a relative humidity control apparatus, a method of operating the apparatus, an immunoassay method and methods of controlling the time course of the relative humidity in a gaseous space and of producing a predetermined volume of a liquid.

In the fields of drug discovery, combinatorial chemistry, screening and synthesis, processes are automated to an increasingly higher degree and are performed with decreasing volumes of sample substance and reagents. It is common practice to combine a multiplicity of single sample containers—named wells in this context—to a larger unit called well plate or titer plate. The well plate typically comprises wells arranged in matrix form. Larger well plates are usually produced as plastic parts. Increasing miniaturization is possible, e.g. by using photo structured glass or silicon microstructures, wherein the wells are formed as cavities or indentations. Titer plates can also have a planar surface, the wells then being separated by a coating forming hydrophobic dams. Titer plates with well volumes of milliliter to microliter are referred to as microtiter plates, titer plates with well volumes in the nanoliter range are referred to as nanotiter plates.

Individual process steps in chemical, biochemical as well as biological processes may comprise reactions at elevated temperatures or may take some time. During this time, a solvent, which in many relevant cases is water, can evaporate from the wells. Thereby the concentration of dissolved substances changes which may have adverse impact on the course of a reaction or the result of a quantitative analysis.

For very small volumes and a large number of wells in a well plate, pipetting a substance into every well may already take such a long time, that a relevant part of the volume initially filled into the wells is already evaporated when the pipetting of all wells is finished.

The rate of evaporation depends—among other parameters—on the free surface of the substance in the well. The smaller the volume in a well, the less favorable is the ratio of the surface to the volume of the sample. Therefore, progress in miniaturization of well plates requires increasingly better control of evaporation of samples.

A known method to counteract this evaporation problem is to cover the openings of the wells by a lid or foil during process steps requiring longer periods. However, the mounting (lidding) and demounting (delidding) of a lid or a foil is a delicate process step that may, if not performed properly, lead to unwanted transfer of sample substance between different wells (cross-contamination). Furthermore, a lid or a foil prevents access to the wells, e.g. by pipette tip of a liquid handling robot. For each pipetting operation, the lid or the foil needs to be removed and put back in place again. In the case of a planar titer plate with drops of sample liquid sitting on top of a plane and being separated only by hydrophobic coating between the wells, the approach of covering the samples by a lid or foils is widely impractical. Either a cover is dangerously close to the sample or the volume enclosed by the lid or foil is too large to prevent evaporation effectively.

A further method is known from the publication DE 10025809 A1. By the device and the method laid open in this publication vapor exchange between a sample and the surrounding atmosphere is controlled by determining the dew point in the surrounding atmosphere und adjusting the temperature of the sample to be close to the dew point. When applying this method, the opening of the wells is not covered and pipetting is possible at any time. This approach has the downside, that the temperature of the samples is not a freely selectable parameter that can be chosen appropriate to the process in question, but rather is determined by the vapor pressure of the solvent—in this case water—in the surrounding of the sample.

The object of the present invention is to provide an apparatus, which reduces undesired evaporation of samples and still enables free access to the samples and allows a choice of the sample temperature. A particular object of the present invention is to provide such an apparatus for samples contained in titer plates, in particular microtiter plates or nanotiter plates.

This object is achieved by a relative humidity control apparatus for control of relative humidity in a gas space according to claim 1. Such a control apparatus comprises a nebulizer source having an outlet for nebulized liquid,
a frame, preferably a frame forming a closed loop, surrounding an open area and comprising an opening arrangement to said open area and in operational flow connection with said outlet,
a flow drive arrangement generating a gas flow from said outlet to said and out of said opening arrangement.

This apparatus solves the object of the invention in a simple and effective way in that a titer plate with liquid samples can be placed in the open area surrounded by the frame. When the apparatus is operated, an atmosphere of controlled relative humidity is produced over the titer plate and evaporation of the samples is reduced. The frame does not block the access to the sample from above and therefore enables free access to the samples. The sample temperature can be chosen freely according to needs of the process to be performed. The inventive apparatus can then be used to adjust the relative humidity around the samples accordingly. An advantage of using a nebulizer lies in the fact that it is largely independent of the temperature.

The operational flow connection may be implemented as an air duct connecting the outlet for nebulized liquid and the opening arrangement of the frame.

The inventive apparatus could be described as an "open humidity chamber".

In one embodiment of the control apparatus according to the invention, which may be combined with any of the embodiments still to be addressed unless in contradiction, said nebulizer source comprises a container and an ultrasonic nebulizer arrangement operationally connected to said container.

The nebulizer source may comprise a container designed to store an amount of water and an ultrasonic nebulizer arranged in the container or attached to the container, such that ultrasonic waves are transmitted into the water and small droplets form above the surface of the water.

In one embodiment of the control apparatus according to the invention, which may be combined with any of the embodiments still to be addressed unless in contradiction, said flow drive arrangement comprises a pressure source generating a pressure gradient from said outlet to said open space via said opening arrangement, preferably a blower, preferably with a blower output operationally connected to an input opening to said container.

In one embodiment of the control apparatus according to the invention, which may be combined with any of the embodiments still to be addressed unless in contradiction, the frame comprises at least one groove, preferably a groove all along said frame, said at least one groove being open towards said open area, and wherein preferably at least a part of said opening arrangement is provided in the base of said groove, facing said open area.

A particular advantage of this embodiment is that it leads to a uniform distribution of humidity in the space enclosed by the frame. The groove forms a channel for the air that is open to its bottom side. The groove guides the air or gas flow along the perimeter of the opening.

The groove may separate a down facing portion of the frame into an outer wall and an inner wall closer to the opening than the outer wall. A lower edge of the inner wall may be located in a higher position than the lower edge of the outer wall at least in a section of the perimeter, such that the groove has a connection to the space enclosed by the frame. An air inlet of the frame may lead into the groove.

In one embodiment of the control apparatus according to the invention, which may be combined with any of the embodiments still to be addressed unless in contradiction, it comprises a second container flow-interconnected between said outlet and said opening arrangement.

The presence of the second container leads to a more stable humidity in the air or gas flow reaching the frame.

In one embodiment of the control apparatus according to the invention, which may be combined with any of the embodiments still to be addressed unless in contradiction, the frame defines a plane and is preferably substantially circular or substantially rectangular.

The basic structure of the frame given, there is a lot of flexibility to adapt the form of the frame and the opening it surrounds to different applications of the apparatus. The perimeter of the opening may have the form of a circle or a rectangle, in particular a rectangle with rounded or chamfered corners. From a fluid dynamical point of view, a rectangular form of the frame having sharp corners may be less favorable than a rectangle with rounded or chamfered corners.

In one embodiment of the control apparatus according to the invention, which may be combined with any of the embodiments still to be addressed unless in contradiction, said open space is one-side limited by a wall one of adjacent to and of on said frame, said wall comprising preferably a titer plate with wells exposed to said open space.

In one embodiment of the control apparatus according to the invention, which may be combined with any of the embodiments still to be addressed unless in contradiction, it comprises a holder for an exchangeable plate said plate on said holder one-side limiting said open space surrounded by said frame.

Such a holder for an exchangeable plate is helpful in cases when a planar object has to be positioned precisely with respect to the frame. The holder may comprise positioning means defining a planar top limit stop. Spring elements may be provided to press a plate that e.g. may be a titer plate in the form of a slide or disc against the positioning means.

In another embodiment of the control apparatus according to the invention, which may be combined with any of the embodiments still to be addressed unless in contradiction, it comprises at least one of at least one humidity sensor and of at least one temperature sensor operationally connected to said open space, at least one of said sensors being preferably provided on or adjacent said frame.

A humidity sensor that is comprised in the apparatus allows to directly monitor relative humidity at a point of interest. The humidity sensor may be placed somewhere in the space enclosed by the frame to monitor the humidity controlled atmosphere created there. It may be used to measure the humidity of the air surrounding the apparatus, and then to derive a power to be delivered to the ultrasound nebulizer or to adapt the volume flow created by the flow drive arrangement based on the measured humidity value. It may also be used to monitor the humidity in the first container, in an air duct or in the second container, if applicable. The humidity sensor may be a capacitive polymer humidity sensor. Capacitive polymer humidity sensors are commercially available and cover large measurement range for humidity and a large working range concerning temperature.

The humidity sensor may be arranged in proximity of the frame in a position facing the opening. In such a position, the humidity values measured by the humidity sensor directly relate to the atmosphere created in the space surrounded by the frame. A position close to the frame helps to allow access to most positions in the opening of the frame. The uniform humidity distribution created by the inventive apparatus allows choosing this position for the humidity sensor. The control apparatus may comprise additional humidity sensors and/or temperature sensors. The combination of a temperature sensor with a humidity sensor in the same position enables temperature dependent calibration and increased precision of the measured humidity. Further sensors may be placed in positions already discussed above.

In another embodiment of the control apparatus according to the invention, which may be combined with any of the embodiments still to be addressed unless in contradiction, said flow drive arrangement comprises at least one of a fan, a piston pump, a rotary vane pump.

In another embodiment of the control apparatus according to the invention, which may be combined with any of the embodiments still to be addressed unless in contradiction, it comprises a source of a dry gas, preferably at least one of a hygroscopic substance and of a pressurized gas tank with dry gas, preferably with at least one of dry air and of nitrogen, and in controllable operational flow connection with said open space, controllable by means of an adjustable flow controller arrangement.

In many relevant cases, the desired relative humidity may be higher than the relative humidity present in the air surrounding the apparatus. The embodiment just described in addition allows producing an atmosphere in the space enclosed by the frame that has a lower relative humidity than the air surrounding the apparatus. This embodiment can even be used to deliberately evaporate liquid sample by keeping the humidity on a very low level.

In a further embodiment of the control apparatus according to the invention, which may be combined with any of the embodiments still to be addressed unless in contradiction, it further comprises a control unit, wherein an input to the control unit is operationally connected to at least one humidity sensor and a control output of said control unit is operationally connected to a control input of at least one of the nebulizer source, of the flow drive arrangement and of a dry gas source to said open space.

The operational connection between the control unit and the nebulizer source may be established by sending control signals to a power supply for an ultrasonic nebulizer. The operational connection between the control unit and the flow drive arrangement may be established by sending control signals to a power supply for a fan. A fully automatic negative feedback control loop can be implemented in this embodiment. The control unit can e.g. comprise a microprocessor. Such a negative feedback control loop can be set up to keep the relative humidity on a predetermined value. A value slightly below the saturation point, e.g. 95% relative humidity, would be a possible choice to reduce the evaporation of sample liquid and at the same time preventing condensation of water on slightly cooler object.

Further in the scope of the invention lies a method of operating the control apparatus according to the invention, wherein pulse width modulation is applied to control the time average power delivered to at least one of the nebulizer source and of the flow drive arrangement.

This method of operating the apparatus can e.g. be carried out in that a constant power is supplied to the nebulizer source and that the flow drive arrangement is periodically switched on and off for an on-time and an off-time, respectively. The ratio between on-time and off-time can repeatedly be adjusted depending on the difference between a measured relative humidity value and a predetermined relative humidity value. If the measured relative humidity value is lower than the predetermined relative humidity value, the on-time is increased, thereby increasing the duty-cycle and the average power supplied to the flow drive arrangement. In this case, pulse width modulation is applied to the flow drive arrangement only. Other possibilities of applying this method are switching on and off the nebulizer source while letting the flow drive arrangement run permanently or applying pulse width modulation to both.

The invention is further directed to a liquid handling robot comprising a control apparatus for control of relative humidity according to the invention.

In an embodiment of the liquid handling robot, it comprises at least one pipetting unit the at least one pipetting unit is operative through said open space.

This embodiment of a liquid handling robot allows keeping a titer plate in the frame of the apparatus for control of relative humidity over longer periods. The pipetting unit be positionable in an automated way. Wells can be accessed individually for pipetting.

In another embodiment of the liquid handling robot, it comprises at least one washing unit having a pair of pipette tips configured to simultaneously dispense into and aspirate from the same well.

With this embodiment, wells can be accessed individually for a washing process involving only one well at a time while samples in other wells are in a reaction or incubation step.

The scope of the invention includes also a method of controlling the time course of the relative humidity in a gaseous space to which an object is exposed and through which the object is treated including a mechanical manipulation in said gaseous space, preferably of controlling said humidity on an at least substantially constant value over a predetermined time span, the method involving the step of placing a frame along said object and in proximity or on said object, feeding nebulized water from said frame into the gaseous space surrounded by said frame and to which said object is exposed, controlling at least one of the amount of nebulized water and of a dry gas fed per time unit to said gaseous space.

In other words, the apparatus according to the invention can e.g. be used to create a humidity controlled atmosphere over an object. More generally than for preventing evaporation, the inventive apparatus can be used to create an atmosphere of controlled humidity.

In an embodiment of the method of controlling the time course of the relative humidity in a gaseous space to which an object is exposed, said controlling is performed by a negative feedback control loop, wherein the prevailing relative humidity in said gaseous space is monitored as a controlled variable.

In an embodiment of the method of controlling the time course of the relative humidity in a gaseous space to which an object is exposed, the object is a titer plate carrying liquid samples, in particular a microtiter plate or a nanotiter plate, wherein preferably form and dimension of the frame match the form and dimension of the outer contour of the titer plate.

Titer plates exist in standardized forms and dimensions, e.g. for rectangular titer plates having 24, 96, 384 or 1536 wells or for discs known as Bio-CD. The dimensions of the opening of the frame of the inventive apparatus can be chosen to match the standardized forms.

In the scope of the invention is an immunoassay method, particular a radioimmunoassay (RIA) method or an immunofluorescence assay (IFA) method, or a magnetic immunoassay (MIA) method, or an enzyme immunoassay (EIA) method or an enzyme linked immunosorbent assay (ELISA) method, or of a genome expression profile analysis method, comprising an incubation step including the inventive method of controlling the time course of the relative humidity in a gaseous space to which an object is exposed.

Incubations steps of samples in the methods listed above may be critical process steps during which a significant amount of liquid can evaporate. These steps can take several minutes to hours and may be performed at elevated temperatures, which increases the evaporation rate. The inventive method is particularly helpful to counteract the evaporation problem in these processes.

Further in the scope of the invention is an immunoassay apparatus, particular a radioimmunoassay (RIA) apparatus or an immunofluorescence assay (IFA) apparatus, or a magnetic immunoassay (MIA) apparatus, or an enzyme immunoassay (EIA) apparatus or an enzyme linked immunosorbent assay (ELISA) apparatus, or of a genome expression profile analysis apparatus, comprising an incubation unit including the control apparatus according to the invention.

Even further in the scope of the invention is a method of producing a predetermined volume of a liquid comprising at least one liquid component, comprising the steps of:

I. providing a predetermined volume of the liquid comprising the at least one liquid component and with a surface exposed to a gaseous atmosphere unsaturated at least with respect to said one liquid component II. manipulating said liquid of said volume during a predetermined manipulation time exposed to said atmosphere and III. maintaining said volume of liquid constant during said time span by providing a buffer-atmosphere between said volume of liquid and said unsaturated atmosphere, said buffer atmosphere being kept saturated at least with respect to said liquid component by nebulizing a liquid which is equal to said liquid component and feeding said nebulized liquid in a controlled manner upon the surface of said volume.

The method may be aimed at the production of a predetermined volume of liquid containing a reaction product created by a chemical reaction from educts e.g. dissolved in water. The volume of liquid may then be maintained constant during the course of the chemical reaction by creating a humidity saturated atmosphere around the volume of liquid. By maintaining the volume of liquid constant, the time course of the concentration of educts and products of the reaction is not exposed to variations due to different humidity conditions in the unsaturated atmosphere. Therefore constant quality of the resulting product can be achieved by applying the method. The method is applicable to different liquid components of the atmosphere, e.g. water, ethanol or any other solvent.

The invention shall now be further exemplified with the help of figures. The figures show:

FIGS. 4.a) and 4.b) are cross-sectional views through an embodiment of the frame of the apparatus FIG. 4.a) a cross-section along a horizontal plane FIG. 4.b) a cross-section perpendicular to the plane in 4.a).

Figure 1:
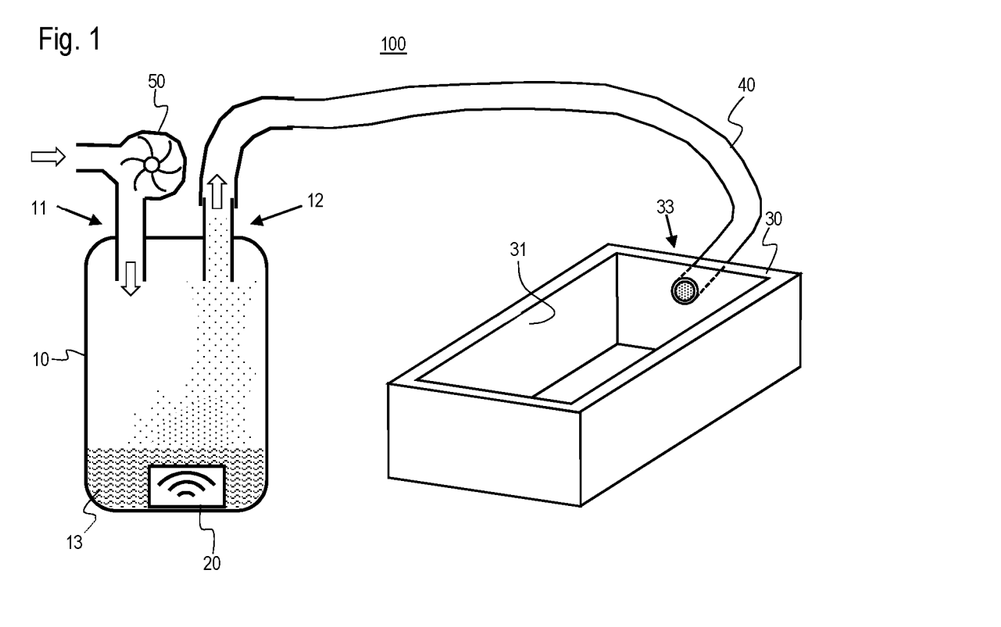
FIG. 1 a schematic view of the apparatus according to the invention.

FIG. 1 shows in a partially cross-sectional, partially perspective view, schematically and simplified, a relative humidity control apparatus according to the invention. A first container 10 contains water 13. Small water droplets are formed above the water surface when an ultrasonic nebulizer 20 is switched on and transmits ultrasonic waves into the water. The ultrasonic nebulizer is arranged in the first container. A flow drive arrangement 50 in form of a pump is placed in front of an air inlet 11 of the first container 10. Air is taken in from the outside of the container and flows into an air duct 40 carrying with it the small water droplets. These small water droplets quickly evaporate, thereby increasing the relative humidity of the air. The air having increased relative humidity flows through an air inlet 33 in the frame 30. The air inlet 33 leads through the outer wall 31 of the frame. In the region enclosed by the frame 30 an equilibrium forms between the humidity of the air flowing through the air inlet of the frame and the humidity of the air surrounding the frame.

Figure 2:
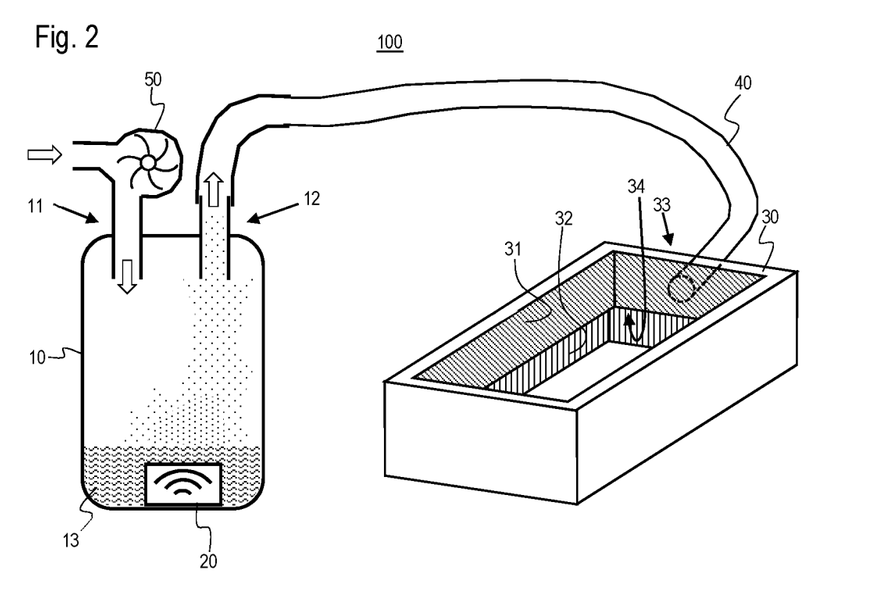
FIG. 2 a schematic view of an embodiment of the apparatus according to the invention.

FIG. 2 shows in a partially cross-sectional, partially perspective view, schematically and simplified, a relative humidity control apparatus of an embodiment of the invention. A first container 10 contains water 13. Small water droplets are formed above the water surface when an ultrasonic nebulizer 20 is switched on and transmits ultrasonic waves into the water. The ultrasonic nebulizer is arranged in the first container. A flow drive arrangement 50 in form of a pump is placed in front of an air inlet 11 of the first container 10. Air is taken in from the outside of the container and flows into an air duct 40 carrying with it the small water droplets. These small water droplets quickly evaporate, thereby increasing the relative humidity of the air. The air having increased relative humidity flows through an air inlet 33 in the frame 30. This air inlet is not directly visible in the current view. Dashed lines in this figure mark the air inlet 33. The air inlet 33 leads into a groove separating an outer wall 31 and an inner wall 32 of the frame. In order to help distinguishing inner wall 31 and outer wall 32, they are marked by oblique and vertical hatching, respectively. The air inlet 33 lies behind the inner wall in this view. The air flows inside the groove along the perimeter of the opening surrounded by the frame 30 and enters into the opening by flowing below the lower edge of the inner wall. In the region enclosed by the frame 30 an equilibrium forms between the humidity of the air flowing through the air inlet of the frame and the humidity of the air surrounding the frame.

Figure 3:
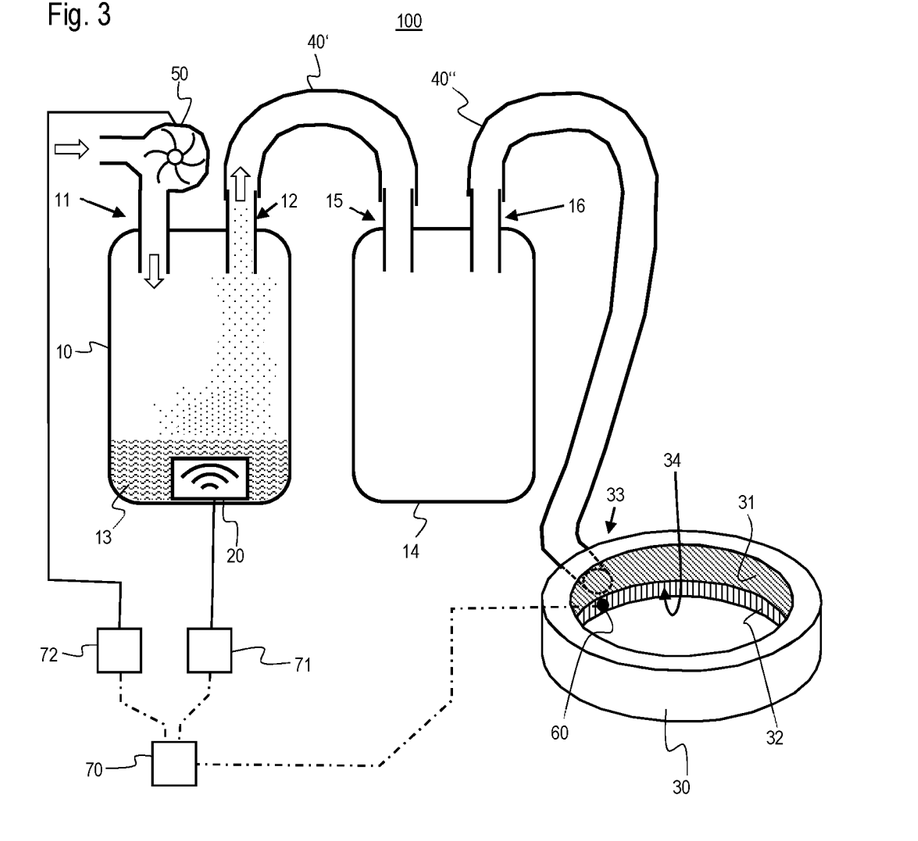
FIG. 3 a schematic view of an embodiment of the apparatus according to the invention.

FIG. 3 shows in a partially cross-sectional, partially perspective view, schematically and simplified, an embodiment of the relative humidity control apparatus according to the invention. In addition to the elements already present in FIG. 2, this embodiment further comprises a second container 14, a humidity sensor 60, a control unit 70, a first power supply 71 and second power supply 72. In this embodiment, the frame 30 has the form of ring such that an opening in the form of a circle results.

In order to help distinguishing inner wall 31 and outer wall 32, they are marked by oblique and vertical hatching, respectively. The air inlet 33 lies behind the inner wall in this view and is marked by dashed lines. The humidity-enriched air leaving the first container through the air outlet 12 is guided into the second container 14 by means of a first section 40' of the air duct. In this second container 14, the residual water droplets have time to evaporate completely. This second container has no other openings than the air inlet 15 and the air outlet 16, such that the same amount of air entering at the air inlet 15 leaves through the air outlet 16 and flows through the second section 40" of the air duct and through the air inlet 33 of the frame 30. A humidity sensor 60 is arranged at the inner wall 31 of the frame 30. The resulting relative humidity can be monitored by means of this humidity sensor. The control unit 70 is operatively connected to the humidity sensor 60, the first power supply 71 and the second power supply 72. This connection is indicated by dash-dotted lines. The operative connection may be implemented as electrical wire connection, but it may as well be a connection established by transmitting optical or radio signals. The control units receives signals from the humidity sensor transmitting the current humidity at the sensor position. Based on this value, the power supplies may be switched on and off or the power of the ultrasonic nebulizer or the volume flow of the pump may be adjusted. This way a negative feedback control loop is possible. With the help of such a negative feedback control loop the relative humidity inside the frame 30 can be kept constant on a predetermined value.

Figure 4:
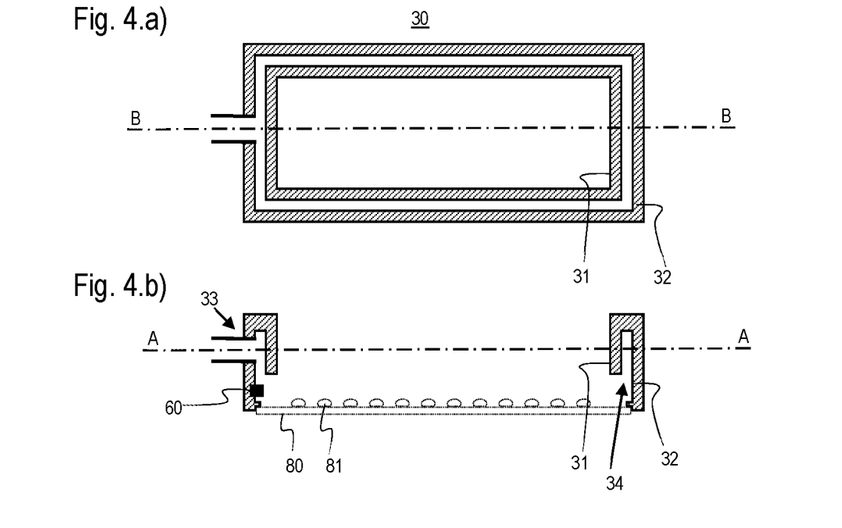

FIGS. 4.a) and 4.b) show cross-sectional views through an embodiment of the frame of the apparatus. In this embodiment, the frame encloses an opening of rectangular form. FIG. 4.a) and FIG. 4.b) show cross sections through two mutually perpendicular planes.

FIG. 4.a) shows a cross-section along a horizontal plane. This horizontal plane lies above the lower edge of the inner wall, such that the plane cuts through both walls, the inner wall 31 and the outer wall 32. The plane also cuts through the air inlet 33 of the frame, which at this level enters into the groove 34 separating the inner and the outer wall. The frame 30 encloses a clear opening in the form of a rectangle. The position marked with a dash-dotted line and the reference sign B is the position of the cross-section shown in FIG. 4.b).

FIG. 4.b) shows the arrangement of the inner wall 31 and the outer wall 32 separated by the groove 34. In dotted lines the possible position of a titer plate 80 carrying liquid samples 81 is shown. In this case, the titer plate is a planar titer plate having hydrophobic coating separating the individual wells. The liquid samples have the form of droplets sitting on the titer plate. The space above the titer plate is supplied by humidity-enriched airflow entering through the air inlet 33 of the frame and being distributed through the groove 34. A humidity sensor 60 is arranged close to the surface of the titer plate and in proximity of the air inlet 33. Positioning means near the lower edge of the outer wall define the position of the titer plate 80. The position marked with a dash-dotted line and the reference sign A is the position of the cross-section shown in FIG. 4.a).

Figure 5:
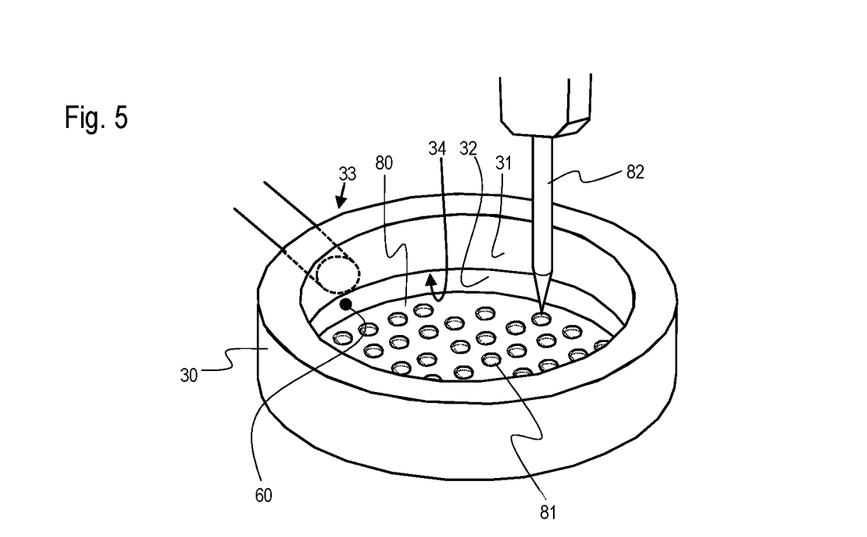
FIG. 5 shows a perspective view of a frame of the apparatus together with a titer plate and a pipette.

FIG. 5 shows a perspective view on a frame 30 of the apparatus together with a titer plate 80 carrying liquid sample 81 droplets and a pipette 82. FIG. 4 illustrates the use of the inventive apparatus to prevent evaporation of samples while allowing free access to the individual sample positions on a titer plate by a pipette. The pipette visible here may be a part of a pipetting unit of a liquid handling robot as well as of a manually operated pipette. Humidity controlled air enters through the air inlet 33 and homogenously distributes in the circular opening of the frame accommodating the titer plate 80. In this embodiment, the titer plate 80 has the form of a disc. A hydrophobic coating (not displayed in the figure) separates the individual wells on the disc from each other and prevents the sample droplets from flowing together. A humidity sensor 60 is arranged on the inside of the frame 30 in a position close to the surface of the titer plate 80. With the humidity sensor placed in this position, it is possible to monitor the relative humidity in the atmosphere surrounding the samples.

Some further technical details not specific to a certain figure are addressed in the following. The ultrasonic nebulizer 20 can e.g. be built as a piezo-electric actuator. A heater and/or a cooler may be comprised in the apparatus to control the temperature of the water in the first container. The flow drive arrangement 50 for creating an airflow through the air duct may be arranged in an other position than shown in FIGS. 1, 2 and 3. It can be positioned anywhere along the path of airflow between the air inlet of the first container to the air inlet of the frame in order to perform its function. The air duct 40 may be a tube made of flexible material. The frame can for example consist of a metallic material and be coated in order to protect it from corrosion. It may be made of stainless steel, or a plastic material.

LIST OF REFERENCE SIGNS

10 First container
11 inlet
12 outlet for nebulized liquid
13 water
14 second container
15 inlet of second container
16 outlet of second container
20 ultrasonic nebulizer arrangement
30 frame
31 outer wall
32 inner wall
33 opening arrangement (of the frame)
34 groove
40 air duct
40' first section of the air duct
40" second section of the air duct
50 flow drive arrangement
60 humidity sensor
70 control unit
71 first power supply
72 second power supply
80 titer plate
81 liquid sample
82 pipette
100 relative humidity control apparatus

The invention claimed is:

1. A relative humidity control apparatus (100) for control of the relative humidity in a gas space, the relative humidity control apparatus comprising
a nebulizer source having an outlet (12) for nebulized liquid,
a frame (30), preferably a frame forming a closed loop, surrounding an open area, which includes said gas space, and said frame comprising an opening arrangement (33) to said open area and in operational flow connection with said outlet,
a flow drive arrangement (50) generating a gas flow from said outlet to said and out of said opening arrangement,
characterized in that
the frame (30) comprises at least one groove (34), said at least one groove being open towards said open area and wherein at least a part of said opening arrangement (33) is provided opposite a wall of said groove (34).

2. The control apparatus of claim 1, said nebulizer source comprising a container (10) and an ultrasonic nebulizer arrangement (20) operationally connected to said container.

3. The control apparatus of one of claims 1, said flow drive arrangement (50) comprising a pressure source generating a pressure gradient from said outlet (12) to said open space via said opening arrangement (33), preferably a blower, preferably with a blower output operationally connected to an input opening (11) to said container (10).

4. The control apparatus (100) according to claim 1, wherein said groove (34) extends all along said frame.

5. The control apparatus (100) according to claim 1 further comprising a second container (14) flow-interconnected between said outlet (12) and said opening arrangement (33).

6. The control apparatus (100) according to claim 1, wherein the frame defines a plane and is preferably substantially circular or substantially rectangular.

7. The control apparatus (100) according to claim 1, wherein said open area is one-side limited by a wall one of adjacent to and of on said frame, said wall comprising preferably a titer plate with wells exposed to said open space.

8. The control apparatus (100) according to claim 1, comprising a holder for an exchangeable plate said plate on said holder one-side limiting said open space surrounded by said frame.

9. The control apparatus (100) according to claim 1, wherein the apparatus comprises at least one of at least one humidity sensor (60) and of at least one temperature sensor operationally connected to said open space, at least one of said sensors being preferably provided on or adjacent said frame.

10. The control apparatus (100) according to claim 1, wherein said flow drive arrangement (50) comprises at least one of a fan, a piston pump, a rotary vane pump.

11. The control apparatus (100) according to claim 1, comprising a source of a dry gas, preferably at least one of a hygroscopic substance and of a pressurized gas tank with dry gas, preferably with at least one of dry air and of nitrogen, and in controllable operational flow connection with said open space, controllable by means of an adjustable flow controller arrangement.

12. The control apparatus (100) according to claim 1, further comprising a control unit (70), wherein an input to the control unit (70) is operationally connected to at least one humidity sensor (60) and a control output of said control unit is operationally connected to a control input of at least one of the nebulizer source, of the flow drive arrangement (50) and of a dry gas source to said open space.

13. Method of operating the control apparatus (100) according to claim 1, wherein pulse width modulation is applied to control the time average power delivered to at least one of the nebulizer source and of the flow drive arrangement (50).

14. The control apparatus of claim 1 including a liquid handling robot comprising the control apparatus (100) for control of relative humidity.

15. The control apparatus according to claim 14 comprising
at least one pipetting unit and
wherein the at least one pipetting unit is operative through said open space.

16. The control apparatus according to claim 14 comprising at least one washing unit having a pair of pipette tips configured to simultaneously dispense into and aspirate from the same well.

17. An immunoassay apparatus, particular a radioimmunoassay (RIA) apparatus or an immunofluorescence assay (IFA) apparatus, or a magnetic immunoassay (MIA) apparatus, or an enzyme immunoassay (EIA) apparatus or an enzyme linked immunosorbent assay (ELISA) apparatus, or of a genome expression profile analysis apparatus, comprising an incubation unit including the control apparatus of claim 1.

* * * * *